United States Patent [19]
Mage

[11] Patent Number: 5,898,468
[45] Date of Patent: *Apr. 27, 1999

[54] FOG-RESISTANT SUNGLASSES INCORPORATING VENTILATION CHANNELS

[75] Inventor: Jerome Jacques Marie Mage, Carlsbad, Calif.

[73] Assignee: Spy Optic, Inc.

[*] Notice: This patent is subject to a terminal disclaimer.

[21] Appl. No.: 08/812,752

[22] Filed: Mar. 6, 1997

Related U.S. Application Data

[63] Continuation-in-part of application No. 08/565,623, Nov. 28, 1995, Pat. No. 5,610,668.

[51] Int. Cl.$^6$ .................................................. G02B 11/08
[52] U.S. Cl. .................................................. 351/62; 351/41
[58] Field of Search .............................. 351/62, 41, 158, 351/156, 157; 2/435, 436, 437

[56] References Cited

U.S. PATENT DOCUMENTS

| | | | |
|---|---|---|---|
| D. 114,800 | 5/1939 | Simon . | |
| D. 118,391 | 1/1940 | Sanders . | |
| D. 134,290 | 11/1942 | Dito et al. . | |
| D. 148,974 | 3/1948 | Bolle | D57/1 |
| D. 151,693 | 11/1948 | Jacobsen | D57/1 |
| D. 169,724 | 6/1953 | Bauer et al. | D57/1 |
| D. 170,435 | 9/1953 | Wiessman | D57/1 |
| D. 189,436 | 12/1960 | Carmichael | D57/1 |
| D. 200,355 | 2/1965 | De Angelis | D57/1 |
| D. 204,210 | 3/1966 | McCulloch | D57/1 |
| D. 204,636 | 5/1966 | Radziwon et al. | D57/1 |
| D. 204,959 | 5/1966 | McCulloch | D57/1 |
| D. 205,093 | 6/1966 | Gaboriault | D57/1 |
| D. 215,761 | 10/1969 | Mitchell | D57/1 |
| D. 218,569 | 9/1970 | McCraken | D57/1 |
| D. 218,953 | 10/1970 | Maiese | D57/1 |
| D. 227,407 | 6/1973 | Marchi | D57/1 F |

(List continued on next page.)

OTHER PUBLICATIONS

Clinton Optical Company, Inc., New York; Jan. 1947; 1 pg.
Optical Journal & Review of Optometry; Apr. 1, 1969; 1 pg.
Welling International; Sep. 1971; 1 pg.
Guild Guide; Sep. 1972; p. 9.
Optometric Weekly; Dec. 14, 1972; p. 7.
Luminos Catolog; Mar. 2, 1973; p. 4.
Optometric Weekly; Jun. 13, 1974; p. 23.
The Optician; Sep. 9, 1977; p. 8.
Lunettes de Soleil; 1983; p. 4.
Accessories; Dec. 1986; front cover.
Yee Fat Optical Manufactory; Mar. 1987; p. 188.
Optician; Apr. 24, 1987; p. 2.
Optician; Apr. 1987; 1 pg.
Optician; May 1988; 1 pg.
Vogue; May 1992; 1 pg.
Macys; Jul. 10, 1996; p. 32.

*Primary Examiner*—Hung Xuan Dang
*Attorney, Agent, or Firm*—Stetina Brunda Garred & Brucker

[57] ABSTRACT

Protective eyeglasses resistant to fogging while being worn by a wearer. The eyeglasses comprise a frame front which spans across the wearer's face and includes a forward side, an aft side, at least one middle portion extending over the wearer's eyes, and a pair of end piece portions near the wearer's temples. Attached to the middle portion of the frame front is at least one lens which is positioned over the wearer's eyes and defines front and back surfaces. Additionally, disposed within the frame front is at least one forwardly directed aperture which defines a ventilation channel for facilitating airflow through the frame front adjacent the lens. The ventilation channel defined by the aperture is sized and configured to facilitate the circulation of air over the back surface of the lens to resist the fogging thereof.

33 Claims, 2 Drawing Sheets

U.S. PATENT DOCUMENTS

| | | | |
|---|---|---|---|
| D. 231,260 | 4/1974 | Jelinek | D57/1 F |
| D. 245,083 | 7/1977 | Zimmermann | D16/65 |
| D. 246,791 | 12/1977 | Shindler | D16/65 |
| D. 289,301 | 4/1987 | Jannard | D16/112 |
| D. 293,450 | 12/1987 | Jannard | D16/102 |
| D. 295,869 | 5/1988 | Lamy | D16/102 |
| D. 311,197 | 10/1990 | Jannard | D16/127 |
| D. 320,402 | 10/1991 | Jannard et al. | D16/127 |
| D. 323,333 | 1/1992 | Jannard et al. | D16/112 |
| D. 323,516 | 1/1992 | Miklitarian | D16/102 |
| D. 324,058 | 2/1992 | Longsdorf et al. | D16/102 |
| D. 324,394 | 3/1992 | Jannard | D16/102 |
| D. 324,528 | 3/1992 | Jannard | D16/102 |
| D. 325,040 | 3/1992 | Jannard | D16/102 |
| D. 326,674 | 6/1992 | Mehringer | D16/102 |
| D. 328,468 | 8/1992 | Jannard | D16/101 |
| D. 329,442 | 9/1992 | Jannard | D16/102 |
| D. 329,445 | 9/1992 | Jannard | D16/116 |
| D. 330,035 | 10/1992 | Jannard | D16/102 |
| D. 330,716 | 11/1992 | Jannard | D16/116 |
| D. 330,903 | 11/1992 | Jannard | D16/116 |
| D. 331,587 | 12/1992 | Jannard et al. | D16/123 |
| D. 331,763 | 12/1992 | Jannard | D16/101 |
| D. 333,145 | 2/1993 | Jannard | D16/101 |
| D. 334,758 | 4/1993 | Reymondet et al. | D16/102 |
| D. 335,887 | 5/1993 | Jannard | D16/101 |
| D. 336,908 | 6/1993 | Jannard | D16/101 |
| D. 339,816 | 9/1993 | Jackson | D16/102 |
| D. 342,534 | 12/1993 | Jannard et al. | D16/102 |
| D. 342,959 | 1/1994 | Jannard et al. | D16/107 |
| D. 343,182 | 1/1994 | Jannard | D16/102 |
| D. 344,281 | 2/1994 | Jannard et al. | D16/102 |
| D. 344,282 | 2/1994 | Hirshman | D16/102 |
| D. 344,742 | 3/1994 | Jannard | D16/112 |
| D. 358,159 | 5/1995 | Lai | 16/312 |
| D. 363,504 | 10/1995 | Arnette | D16/326 |
| D. 365,591 | 12/1995 | Jannard et al. | D16/326 |
| D. 366,666 | 1/1996 | Arnette | D16/325 |
| D. 366,890 | 2/1996 | Arnette | D16/326 |
| D. 366,891 | 2/1996 | Arnette | D16/326 |
| D. 368,108 | 3/1996 | Lei | D16/326 |
| D. 376,810 | 12/1996 | Ohie | D16/326 |
| 2,042,400 | 5/1936 | Hon | 88/41 |
| 2,778,270 | 1/1957 | Pomerance | 88/41 |
| 3,015,987 | 1/1962 | Harrison | 88/41 |
| 4,240,718 | 12/1980 | Wichers | 351/62 |
| 4,447,914 | 5/1984 | Jannard | 2/432 |
| 4,515,448 | 5/1985 | Tackles | 351/41 |
| 4,571,748 | 2/1986 | Carroll et al. | 2/436 |
| 4,665,598 | 5/1987 | Murai et al. | 29/20 |
| 4,707,863 | 11/1987 | McNeal | 2/436 |
| 4,716,601 | 1/1988 | McNeal | 2/434 |
| 4,730,915 | 3/1988 | Jannard | 351/47 |
| 4,826,309 | 5/1989 | VanNeste | 351/114 |
| 4,859,048 | 8/1989 | Jannard | 351/159 |
| 4,867,550 | 9/1989 | Jannard | 351/47 |
| 5,054,903 | 10/1991 | Jannard et al. | 351/123 |
| 5,137,342 | 8/1992 | Jannard et al. | 351/123 |
| 5,208,614 | 5/1993 | Jannard | 351/41 |
| 5,249,001 | 9/1993 | Jannard | 351/123 |
| 5,303,428 | 4/1994 | Pernicka | 216/452 |
| 5,363,512 | 11/1994 | Grabos, Jr. et al. | 216/436 |
| 5,583,584 | 12/1996 | Friedman | 351/52 |
| 5,594,511 | 1/1997 | Lin | 351/116 |
| 5,602,603 | 2/1997 | Bonet | 351/41 |
| 5,610,668 | 3/1997 | Mage | 351/62 |
| 5,642,178 | 6/1997 | Leonardi et al. | 351/111 |

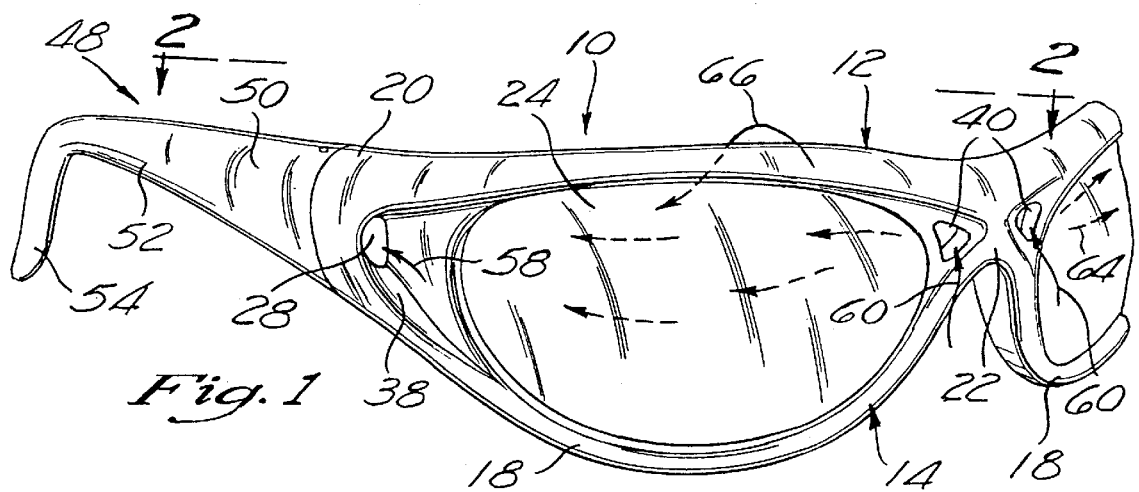
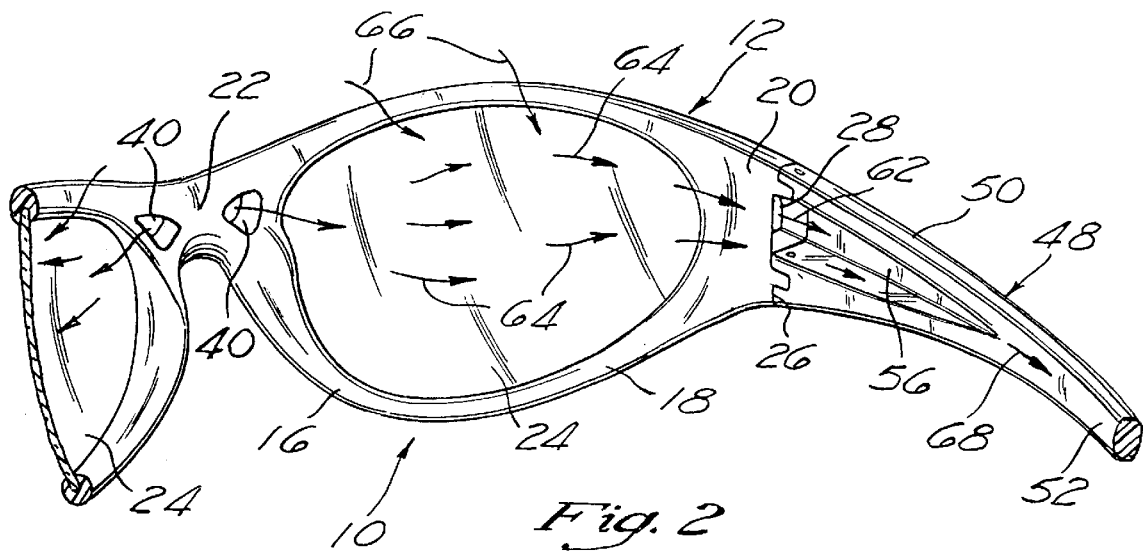

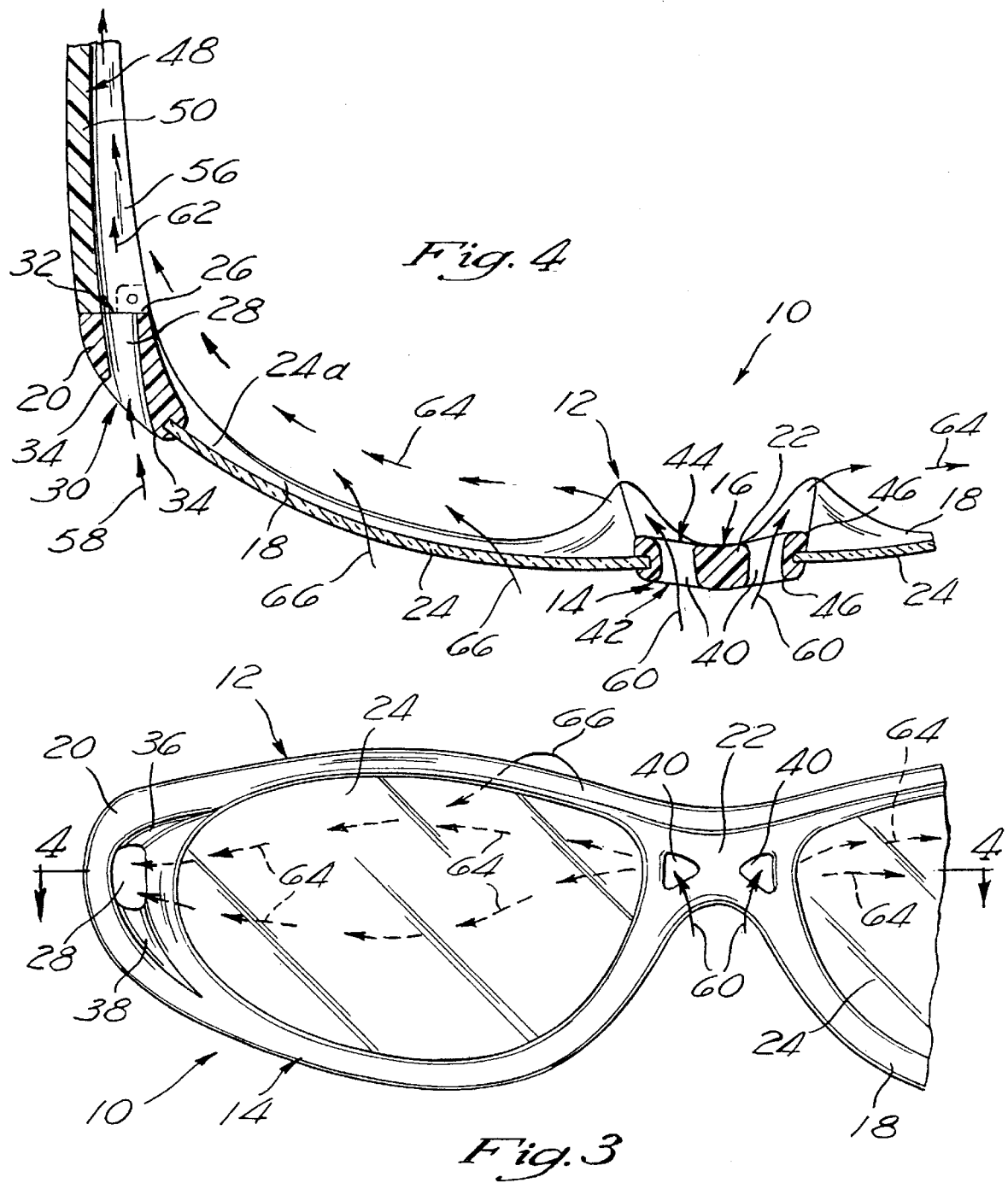

FOG-RESISTANT SUNGLASSES INCORPORATING VENTILATION CHANNELS

The present application is a continuation-in-part of U.S. application Ser. No. 08/565,623 now U.S. Pat. No. 5,610,668 entitled FOG-RESISTANT SUNGLASSES INCORPORATING VENTILATION CHANNELS filed Nov. 28, 1995.

FIELD OF THE INVENTION

The present invention relates generally to protective eyeglasses, and more particularly to sunglasses which incorporate a ventilation channel to promote air circulation behind the lenses thereof so as to minimize or prevent the fogging of the lenses.

BACKGROUND OF THE INVENTION

Protective eyewear or eyeglasses (e.g., sunglasses) having tinted lenses are commonly used in connection with various sports and other activities to protect the participant's eyes. Eye protection is especially needed when the sport or other activity involves unshielded high-speed travel wherein the eyes are susceptible to being impacted by small particles of foreign matter at velocities which equal the rate of travel. Examples of such sporting activities wherein eye protection is recommended include downhill skiing, snowmobiling, cycling, jet skiing and motorcycle racing to keep snow, water, dust, insects, small rocks, etc., out of the participant's eyes.

When protective eyeglasses are used in relation to the above-identified activities, a well-known problem that is often encountered is the fogging or misting, i.e., the build-up of condensation, on the inside surfaces of the lenses. The fogging problem is particularly severe when the wearer is warm and/or perspiring, with the outdoor environment being cool and/or damp. As will be recognized, the fogging of the lenses of the eyeglasses interferes with the wearers vision, and thus presents a potentially hazardous condition.

The problem of lens fogging has been recognized in the prior art wherein several solutions have been proposed to prevent such fogging from occurring. More particularly, in the prior art there are thermal lenses which each consist of a single lens of increased thickness. The increased thickness of the thermal lenses is operative to isolate the outside surfaces of the lenses exposed to the cooler air from the inside surfaces of the lenses which are exposed to the warmer air. Also known in the prior art are double glass lenses, each of which consists of a pair of lens halves separated by an intermediate air-filled space or void. The double glass lenses are also operative to facilitate the isolation of the outermost and innermost surfaces of the lenses from each other. However, the prior art thermal and double glass lenses significantly add to the bulk and weight of the eyeglasses in which they are used, and thus are uncomfortable to wear and not desirable for use in relation to sports activities.

There is also known in the prior art various coatings which are applied to the inside surfaces of the lenses for purposes of immediately condensing or absorbing any mist or fog which accumulates on the inside surfaces. However, such coatings are only effective for an extremely limited duration of time, with the inside surfaces of the glasses periodically needing to be dried in some manner.

It has been recognized in the prior art that the most effective manner of preventing the fogging or misting of the lenses of eyeglasses is to improve air circulation behind the lenses thereof, i.e., exhausting the warm humid air and replacing it with cool drier air. To facilitate such air exchange, there has been developed in the prior art eyeglasses incorporating miniature fans powered by portable batteries carried by the user. However, the eyewear incorporating these miniature fans is extremely complex and costly to manufacture, and is also bulky and of high weight. There has also been developed in the prior art eyeglasses which include ventilation ports disposed within various locations about the periphery of the frame so as to surround the lenses thereof. However, in these prior art eyeglasses, because of the manner in which the ventilation ports are configured and/or oriented, they typically provide either too little or too great a rate of air flow therethrough. Insufficient air flow through the ventilation ports makes the inclusion of the ventilation ports in the frame largely ineffective for purposes of preventing the fogging of the lenses. At the other extreme, too great a rate of air flow through the ventilation ports results in a pressure build-up or in uncomfortably high "winds" across the wearer's eyes. Moreover, the ventilation ports included in the prior art eyeglasses are often sized and configured in a manner wherein foreign manner, e.g., dust, can pass therethrough into the wearer's eyes.

In view of the foregoing, there exists a need for eyeglasses which can safely and adequately protect a wearer's eyes and are resistant to fogging. Such eyeglasses should be simple in construction and thus inexpensive to manufacture, and should further be lightweight so as not to unduly interfere with the wearer's participation in a certain sports activity.

SUMMARY OF THE INVENTION

In accordance with the present invention, there is provided protective eyeglasses which are adapted to be resistant to fogging while being worn by a wearer. The eyeglasses comprise a frame front which spans across the wearer's face and includes forward and aft sides. The frame front further includes a pair of middle portions which extend over the wearer's eyes, and a pair of end piece portions adjacent the wearer's temples. Attached to respective ones of the middle portions of the frame front is a pair of lenses which are positioned over the wearer's eyes and define front and back surfaces. Additionally, disposed within respective ones of the end piece portions of the frame front is a pair of end piece apertures which are forwardly directed and define ventilation channels for facilitating airflow through the frame front adjacent the lenses. The ventilation channels defined by the end piece apertures are sized and configured to facilitate the circulation of air over the back surfaces of the lenses to resist the fogging thereof.

In the preferred embodiment, the middle portions of the frame front are integrally connected to each other by a bridge portion which includes a pair of bridge apertures disposed therein. The bridge apertures of the eyeglasses define additional ventilation channels within the frame front. Each of the ventilation channels defined by the end piece apertures and the bridge apertures includes a forward end at the forward side of the frame front, an aft end at the aft side of the frame front, and a central portion between the forward and aft ends. The forward end of each ventilation channel is partially defined by rounded corners formed within the frame front to promote laminar airflow therethrough. Additionally, the forward ends of those ventilation channels defined by the end piece apertures are further partially defined by a pair of ramps formed within the frame front to further promote laminar airflow therethrough.

In the present eyeglasses, the end piece apertures each comprise an elongate, vertically oriented slot which is formed within a respective one of the end piece portions of the frame front. Additionally, each of the end piece apertures defines a central axis which is substantially parallel to the forward line of sight of the wearer, with the end piece apertures further being positioned outwardly beyond the wearer's eyes to prevent debris passing therethrough from entering the wearer's eyes.

The eyeglasses constructed in accordance with the present invention further comprise a pair of elongate temple members which are pivotally connected to the frame front. The temple members each preferably comprise a butt portion which is pivotally connected to a respective one of the end piece portions of the frame front, with the butt portion itself defining inner and outer surfaces. The butt portion transitions into a shank portions of decreased width, with the shank portion in turn transitioning into a downwardly bent ear piece portion of decreased width. Each ear piece portion is sized and configured to rest upon one of the wearer's ears to maintain the eyeglasses in position upon the wearer's face. The maximum widths of the butt portions of the temple members are substantially equal to the widths of the outboard edges of the end piece portions to which the butt portions are pivotally connected. Additionally, the forward side of the frame front and the outer surfaces of the butt portions of the temple members are substantially flush with each other, as are the inner surfaces of the butt portions and the aft side of the frame front.

In the preferred embodiment, each of the temple members further comprises an elongate ventilation slot which is disposed within the inner surface of the butt portion and communicates with the ventilation channel defined by a respective one of the end piece apertures disposed within the frame front. Each ventilation slot is sized and configured to promote the laminar flow of air passing through the corresponding ventilation channel along the temple member. In this respect, each ventilation slot is of gradually decreasing width and depth as it extends toward the shank portion of the temple member.

In the preferred embodiment, the middle portions of the frame front are themselves arcuately contoured to facilitate airflow about the frame front. Additionally, both the frame front and the lenses preferably have generally concave configurations to facilitate the wrapping of the eyeglasses around the wearer's eyes and to promote laminar airflow around the wearer's face. The height of the end piece portions of the frame front is preferably at least half of the maximum height of the lenses, with the lenses themselves being darkly tinted and fabricated to be of sufficient thickness to prevent the inadvertant fracturing thereof when impacted by debris. The lenses may alternatively be transparent, or fabricated from a material which progressively darkens when exposed to ultraviolet radiation.

BRIEF DESCRIPTION OF THE DRAWINGS

These, as well as other features of the present invention, will become more apparent upon reference to the drawings wherein:

FIG. 1 is a partial front perspective view of the eyeglasses of the present invention, illustrating the manner in which air is circulated therethrough;

FIG. 2 is a partial rear perspective view of the eyeglasses of the present invention taken along line 2—2 of FIG. 1, illustrating the manner in which air is circulated therethrough;

FIG. 3 is a partial front elevational view of the eyeglasses of the present invention, illustrating the manner in which air is circulated therethrough; and FIG. 4 is partial cross-sectional view taken along line 4—4 of FIG. 3, further illustrating the manner in which air is circulated through the eyeglasses of the present invention.

DETAILED DESCRIPTION OF THE PREFERRED EMBODIMENT

Referring now to the drawings wherein the showings are for purposes of illustrating a preferred embodiment of the present invention only, and not for purposes of limiting the same, FIGS. 1 and 2 perspectively illustrate the protective eyeglasses 10 constructed in accordance with the present invention. As will be discussed in more detail below, the eyeglasses 10 of the present invention are specifically adapted to be resistant to fogging. Additionally, as shown in accompanying FIGS. 1–4, the eyeglasses 10 are preferably in the form of sunglasses. However, those of ordinary skill in the art will recognize that the present invention is also applicable to other types of eyeglasses or eyewear, including eyeglasses incorporating a single, unitary lens, as well as goggles.

Referring now to FIGS. 1–4, the eyeglasses 10 of the present invention comprise a frame front 12 which, when the eyeglasses 10 are worn by a wearer, are sized and configured to span across the wearer's face. The frame front 12 includes a front or forward side 14, a back or aft side 16, a pair of middle portions 18, and a pair of end piece portions 20. The middle portions 18 are integrally connected to each other by a bridge portion 22 of the frame front 12, with each of the middle portions 18 accommodating a lens 24 of the eyeglasses 10. As will be recognized, when the eyeglasses 10 are worn by the wearer, the middle portions 18 extend over the wearer's eyes, with the lenses 24 disposed therewithin thus being positioned over the wearer's eyes. Additionally, the end piece portions 20 are positioned adjacent the wearer's temples, with each of the end piece portions 20 defining an outboard edge 26, the use of which will be described in more detail below.

In the preferred embodiment, the frame front 12 of the eyeglasses 10 further includes a pair of end piece apertures 28 which are disposed within respective ones of the end piece portions 20 thereof. The end piece apertures 28 each define a forward end 30 at the forward side 14 of the frame front 12, an aft end 32 at the aft side 16 of the frame front 12, and a central portion disposed between the forward and aft ends 30, 32.

As seen in FIGS. 1–4, each of the end piece apertures 28 comprises an elongate, vertically oriented slot defining a central axis which extends in substantially parallel relation to the forward line of sight of the wearer of the eyeglasses 10. As best seen in FIG. 4, the forward end 30 of each end piece aperture 28, and in particular the longitudinal edges thereof, is defined by rounded corner regions 34 formed within the frame front 12. Additionally, as seen in FIGS. 1 and 3, the lateral sides of each end piece aperture 28 are defined by a sloped upper surface or upper ramp 36 and a sloped lower surface or lower ramp 38. In this respect, the inclusion of the upper and lower ramps 36, 38 in the frame front 12 facilitates the gradual reduction in the cross-sectional area of each end piece aperture 28 as it extends toward its aft end 32 at the aft side of the frame front 12. Moreover, the inclusion of the rounded corner regions 34 and upper and lower ramps 36, 38 with each end piece aperture 28 promotes the laminar flow of air therethrough for reasons which will be discussed in more detail below.

In addition to the end piece apertures 28, disposed within the bridge portion 22 of the frame front 12 is a spaced pair of bridge apertures 40, each of which has a generally triangular configuration and defines a central axis which extends in substantially parallel relation to the forward line of sight of the wearer of the eyeglasses 10. Like the end piece apertures 28, each of the bridge apertures 40 defines a forward end 42, an aft end 44, and a central portion which is disposed between the forward and aft ends 42, 44. In the preferred embodiment, the forward and aft ends 42, 44 of each bridge aperture 40 are defined by rounded corner regions 46 of the frame front 12 which promote the laminar flow of air through the bridge apertures 40.

In the eyeglasses 10 of the present invention, the forwardly directed end piece apertures 28 and bridge apertures 40 define ventilation channels for facilitating airflow through the frame front 12 adjacent the lenses 24 thereof. As will also be discussed in more detail below, the ventilation channels defined by the end piece and bridge apertures 28, 40 are sized and configured to facilitate the circulation of air over the back surfaces 24a of the lenses 24 to resist the fogging thereof.

Referring now to FIGS. 1, 2 and 4, the eyeglasses 10 of the present invention further comprise an identically configured pair of elongate temple members 48 which are pivotally connected to the frame front 12, and more particularly to respective ones of the outboard edges 26 of the end piece portions 20. Each of the temple members 48 comprises a butt portion 50 which is pivotally connected to the outboard edge 26 of a respective end piece portion 20. In the preferred embodiment, the maximum width of the butt portion 50 is substantially equal to the width of the outboard edge 26 to which it is pivotally connected. Additionally, as best seen in FIGS. 2 and 4, when the butt portion 50 is pivotally connected to the outboard edge 26 of the end piece portion 20, the outer surface of the butt portion 50 is substantially flush with the forward side 14 of the frame front 12, with the inner surface of the butt portion 50 being substantially flush with the aft side 16 of the frame front 12. The butt portion 50 of each temple member 48 transitions into a reduced width shank portion 52 thereof. The shank portion 52 of each temple member 48 itself transitions into a reduced width earpiece portion 54 which has a downwardly bent configuration and is sized and configured to rest upon one of the wearer's ears to maintain the eyeglasses 10 in position upon the wearer's face.

As best seen in FIGS. 2 and 4, disposed within the inner surface of the butt portion 50 of each temple member 48 is an elongate ventilation slot 56 which, when the temple member 48 is pivotally connected to the outboard edge 26, communicates with the ventilation channel defined by a respective one of the end piece apertures 28 formed within the frame front 12. Each ventilation slot 56 has a generally triangular configuration, and is of gradually decreasing width and depth as it extends toward the shank portion 52 of the temple member 48. As will also be discussed in more detail below, the ventilation slots 56 are sized and configured to cooperate with the end piece apertures 28 in a manner promoting the laminar flow of air passing through the ventilation channels along the temple members 48.

As best seen in FIG. 4, in the preferred embodiment both the frame front 12 and the lenses 24 disposed therein have arcuate, generally concave configurations to create the effect of the eyeglasses 10 "wrapping" around the wearer's eyes and head when worn by the wearer. In addition to creating the wrapping effect, the arcuate contours of the frame front 12 and lenses 24 promotes the laminar flow of air around the wearer's face, as well as airflow about the middle portions 18 of the frame front 12 into the spaces or voids defined between the back surfaces 24a of the lenses 24 and the wearer's eyes. To further streamline the eyeglasses 10, the end piece portions 28 of the frame front 12 are preferably sized having a height which is at least half of the maximum height of the lenses 24.

As will be recognized, when the eyeglasses 10 are worn by the wearer, the bridge portion 22 of the frame front 12 is rested upon the bridge of the wearer's nose, with the lower edges of the middle portions 18 typically resting against the portions of the wearer's cheeks adjacent the eyes. Additionally, the downwardly bent eye piece portions 54 of the temple members 48 are rested upon respective ones of the wearer's ears. As previously indicated, when the eyeglasses 10 are worn in the proper manner, air filled spaces or voids are defined between the back surfaces 24a of the lenses 24 and the wearer's eyes.

In the preferred embodiment, the frame front 12 and temple members 48 are fabricated from a light weight, shatter-proof plastic material. The lenses 24 are themselves preferably darkly tinted, or fabricated from a material having a tint which adjusts in accordance with different brightness levels. Those of ordinary skill in the art will recognize that the lenses 24 may be fabricated from a variety of different materials, and may also be transparent rather than tinted. However, it is contemplated that the lenses 24 will be fabricated having a sufficient thickness to prevent the inadvertant fracturing thereof when impacted by debris. In this respect, the frame front 12 is sized such that the end piece apertures 28 disposed within the end piece portions 20 are oriented outwardly relative to the wearer's eyes so that any debris passing through the ventilation channels defined by the end piece apertures 28 will not directly enter the wearer's eyes.

Having thus described the components comprising the eyeglasses 10, the manner in which the eyeglasses 10 are resistant to fogging will now be described with reference to the arrows shown in FIGS. 1–4. As previously indicated, when the eyeglasses 10 are worn in the proper manner, spaces or voids are defined between the back surfaces 24a of the lenses 24 and the wearer's eyes. These spaces are partially enclosed by the contact of the lower edges of the middle portions 18 against the wearer's cheeks and the bridge portion 22 against the bridge of the wearer's nose. During the wearer's participation in a sports activity, the wearer's body, through physical exertion, is generating heat, with the wearer's breathing dispelling warm, humid air in the vicinity of the eyeglasses 10. As will be recognized, the increase in the wearer's body temperature and resultant perspiration tends to cause the air within the spaces between the wearer's eyes and the back surfaces 24a of the lenses 24 to increase both in temperature and moisture content. Such increase in temperature and moisture content of the air behind the lenses 24, when coupled with the presence of cool, drier air at the front surfaces of the lenses 24, results in the formation of condensation on the back surfaces 24a of the lenses 24, i.e., the "fogging" of the lenses 24.

When the wearer of the eyeglasses 10 is traveling forward through relatively cool, dry air at a relatively high rate of speed, the cool outside air flows through the ventilation channels defined by the end piece apertures 28 and bridge apertures 40. More particularly, as seen in FIGS. 1 and 4, air enters the end piece apertures 28 in the direction designated by the arrows 58, and enters the bridge apertures in the direction designated by the arrows 60. Air passing through the end piece apertures 28 flows into and through respective ones of the ventilation slots 56 in the direction designated by the arrows 62. The air within the spaces between the back surfaces 24a of the lenses 24 and the wearer's eyes tends to be drawn into the flow of air identified by the arrows 62, which in turn causes the air entering such spaces via the bridge apertures 40 to be drawn across the back surfaces 24a of respective ones of the lenses 24 in the direction designated by the arrows 64. Additionally, due to the streamlined configuration of the frame front 12, air is also drawn over the top edges of the middle portions 18 across the back surfaces 24a of the lenses 24 in the direction designated by the arrows 66. Due to the configuration of the ventilation slots 56, the air flowing outwardly within the spaces along the back surfaces 24a combines with the air flowing through the end piece apertures 28 into the ventilation slots 56, with such combined air ultimately flowing along respective ones of the temple members 48 in the direction designated by the arrow 68 shown in FIG. 2.

As will be recognized, the drawing of the air within the spaces between the lenses 24 and the wearer's eyes into the flow through the end piece apertures 28 and ventilation slots 56 effectively reduces the pressure in such spaces, thus facilitating the circulation of the air entering the spaces via the bridge apertures 40 and over the top edges of the middle portions 18 across the back surfaces 24a of the lenses 24 in the aforementioned manner. The exchange of the cool, drier air for the warm moist air in the spaces and circulation of the cool, drier air across the back surfaces 24a of the lenses 24 prevents the formation of condensation (i.e., the "fogging") of the lenses 24. As such, the reduction or elimination of fogging of the lenses 24 is provided, though the eyeglasses 10 are lightweight in construction and of relatively low cost to manufacture.

Though not shown, it is contemplated that the central portions of the end piece apertures 28 and/or bridge apertures 40 may be formed so as to be narrower than the forward and aft ends thereof. In this respect, the end piece apertures 28 and/or bridge apertures 40 may each have a generally "hourglass" shape. This particular configuration of each of the end piece apertures 28 and/or bridge apertures 40 aids in creating a "venturi" effect in the flow of air therethrough. The term "venturi" is generally defined as a tube having a narrow region in the middle with flared or widened ends. The venturi effect is the result of Bernoulli's Principle which establishes that the flow rate of a fluid will increase and pressure will decrease in the narrowed region of the venturi. This "venturi" effect occurring within the ventilation channels defined by the end piece apertures 28 and/or bridge apertures 40 could be used to facilitate even increased circulation of air behind the lenses 24.

Additional modifications and improvements of the present invention may also be apparent to those skilled in the art. Thus, the particular combination of parts described and illustrated herein is intended to represent only one embodiment of the present invention, and is not intended to serve as limitations of alternative devices within the spirit and scope of the invention.

What is claimed is:

1. Protective eyeglasses resistant to fogging while being worn by a wearer, said eyeglasses comprising:
    a frame front which spans across the wearer's face, said frame front including a forward side, an aft side, at least one middle portion extending over the wearer's eyes, and a pair of end piece portions near the wearer's temples;
    at least one lens attached to the middle portion of the frame front and positioned over the wearer's eyes, said lens defining front and back surfaces; and
    at least one forwardly directed aperture disposed within the frame front and defining a central axis which extends in substantially parallel relation to the wearer's forward line of sight, said aperture forming a ventilation channel for facilitating air flow through the frame front adjacent the lens;
    wherein the size and configuration of the ventilation channel and extension thereof along the central axis facilitates the circulation of air over the back surface of the lens to resist the fogging thereof.

2. The protective eyeglasses of claim 1 wherein said frame front includes a pair of middle portions connected by a bridge portion and said eyeglasses comprise a pair of lenses attached to respective ones of the middle portions.

3. The protective eyeglasses of claim 2 wherein said at least one aperture comprises a pair of end piece apertures disposed within respective ones of the end piece portions of the frame front for facilitating the circulation of air over the back surfaces of the lenses.

4. The eyeglasses of claim 3 wherein the ventilation channel defined by each of the end piece apertures defines a forward end at the forward side of the frame front, an aft end at the aft side of the frame front, and a central portion between the forward and aft ends, the forward end of each ventilation channel defined by the end piece apertures being partially defined by a pair of ramps formed within the frame front to promote laminar air flow therethrough.

5. The eyeglasses of claim 4 wherein the forward end of each ventilation channel defined by the end piece apertures is partially defined by rounded corners formed within the frame front to promote laminar air flow therethrough.

6. The protective eyeglasses of claim 3 wherein said at least one aperture further comprises at least one bridge aperture disposed within the bridge portion of the frame front.

7. The protective eyeglasses of claim 6 wherein said at least one bridge aperture comprises a pair of bridge apertures disposed within the bridge portion of the frame front.

8. The eyeglasses of claim 7 wherein each of the ventilation channels defined by the bridge apertures defines a forward end at the forward side of the frame front, an aft end at the aft side of the frame front, and a central portion between the forward and aft ends, the forward end of each ventilation channel defined by the bridge apertures being partially defined by rounded corners formed within the frame front to promote laminar air flow therethrough.

9. The eyeglasses of claim 3 wherein the end piece apertures each comprise an elongate, vertically oriented slot formed within a respective one of the end piece portions of the frame front.

10. The eyeglasses of claim 3 wherein the end piece apertures are positioned outwardly beyond the wearer's eyes to prevent debris passing therethrough from entering the wearer's eyes.

11. The eyeglasses of claim 3 further comprising a pair of elongate temple members pivotally connected to said frame front, each of said temple members comprising:
    a butt portion pivotally connected to a respective one of the end piece portions of the frame front, said butt portion defining inner and outer surface;
    a shank portion; and
    a ear piece portion sized and configured to rest upon one of the wearer's ears to maintain the eyeglasses in position upon the wearer's face.

12. The eyeglasses of claim 11 wherein the end piece portions of the frame front each define an outboard edge, with the widths of the butt portions of the temple members and the widths of the outboard edges of the end piece portions being substantially equal.

13. The eyeglasses of claim 12 wherein the widths of the butt portions of the temple member exceed the widths of the shank portions thereof.

14. The eyeglasses of claim 13 wherein the widths of the shank portions of the temple members exceed the widths of the ear piece portions thereof.

15. The eyeglasses of claim 11 wherein the forward side of the frame front and the outer surfaces of the butt portions of the temple members are substantially flush with each other.

16. The eyeglasses of claim 11 wherein the aft side of the frame front and the inner surfaces of the butt portions of the temple members are substantially flush with each other.

17. The eyeglasses of claim 11 wherein the ear piece portion of each of the temple member has a downwardly bent configuration.

18. The eyeglasses of claim 11 wherein each of the temple members further comprises:

an elongate ventilation slot disposed within the inner surface of the butt portion and communicating with the ventilation channel defined by a respective one of the end piece apertures disposed within the frame front;

said ventilation slot being sized and configured to promote the laminar flow of air passing through the ventilation channel along the temple member.

19. The eyeglasses of claim 18 wherein said ventilation slot is of gradually decreasing width and depth as it extends toward the shank portion of the temple member.

20. The eyeglasses of claim 3 wherein the middle portions of the frame front are arcuately contoured to facilitate airflow about the frame front.

21. The eyeglasses of claim 3 wherein the height of the end piece portions of the frame front is at least half of the maximum height of the lenses.

22. The eyeglasses of claim 3 wherein the frame front and the lenses are generally concave to facilitate the wrapping of the eyeglasses around the wearer's eyes and promote laminar airflow around the wearer's face.

23. The eyeglasses of claim 3 wherein the lenses are darkly tinted.

24. The eyeglasses of claim 3 wherein the lenses are fabricated to be of sufficient thickness to prevent the inadvertant fracturing thereof when impacted by debris.

25. Protective eyeglasses resistant to fogging while being worn by a wearer, said eyeglasses comprising:

a frame front which spans across the wearer's face, said frame front including a forward side, an aft side, at least one middle portion extending over the wearer's eyes, and a pair of end piece portions near the wearer's temples;

at least one lens attached to the middle portion of the frame front and positioned over the wearer's eyes, said lens defining front and back surfaces; and a pair of forwardly directed end piece apertures disposed within respective ones of the end piece portions of the frame front, said end piece apertures each defining a central axis which extends in generally parallel relation to the wearer's forward line of sight, and forming ventilation channels for facilitating airflow through the frame front adjacent the lens;

wherein the size and configuration of the ventilation channels and extension thereof along respective ones of the central axes facilitates the circulation of air over the back surface of the lens to resist the fogging thereof.

26. The protective eyeglasses of claim 25 wherein said frame front includes a pair of middle portions connected by a bridge portion and said eyeglasses comprise a pair of lenses attached to respective ones of the middle portions.

27. The protective eyeglasses of claim 26 further comprising a pair of bridge apertures disposed within the bridge portion of the frame front.

28. The eyeglasses of claim 27 wherein the ventilation channels defined by the end piece apertures and the bridge apertures each define a forward end at the forward side of the frame front, an aft end at the aft side of the frame front, and a central portion between the forward and aft ends, the forward end of each ventilation channel being partially defined by rounded corners formed within the frame front to promote laminar airflow therethrough.

29. The eyeglasses of claim 27 wherein each of the ventilation channels defined by the end piece apertures each define a forward end at the forward side of the frame front, an aft end at the aft side of the frame front, and a central portion between the forward and aft ends, the forward end of each ventilation channel being partially defined by a pair of ramps formed within the frame front to promote laminar airflow therethrough.

30. The eyeglasses of claim 25 further comprising a pair of elongate temple members pivotally connected to said frame front, each of said temple members comprising:

a butt portion pivotally connected to a respective one of the end piece portions of the frame front, said butt portions defining inner and outer surfaces;

a shank portion; and a ear piece portion sized and configured to rest upon one of the wearer's ears to maintain the eyeglasses in position upon the wearer's face.

31. The eyeglasses of claim 30 wherein each of the temple members further comprises:

an elongate ventilation slot disposed within the inner surface of the butt portion and communicating with the ventilation channel defined by a respective one of the end piece apertures disposed within the frame front;

said ventilation slot being sized and configured to promote the laminar flow of air passing through the corresponding ventilation channel along the temple member.

32. The eyeglasses of claim 31 wherein said ventilation slot is of gradually decreasing width and depth as it extends toward the shank portion of the temple member.

33. Protective eyeglasses resistant to fogging while being worn by a wearer, said eyeglasses comprising:

a frame front which spans across the wearers face, said frame front including a forward side, an aft side, a pair of middle portions extending over the wearer's eyes, a bridge portion connecting the middle portions, and a pair of end piece portions near the wearer's temples;

a pair of lenses attached to respective ones of the middle portions of the frame front and positioned over the wearer's eyes, said lenses each defining front and back surfaces;

a pair of end piece apertures disposed within respective ones of the end piece portions of the frame front, said end piece apertures defining ventilation channels for facilitating air flow through the frame front adjacent the lenses; and at least one bridge aperture disposed within the bridge portion of the frame front and defining a ventilation channel for facilitating air flow through the frame front adjacent the lenses;

wherein the ventilation channels defined by the end piece apertures and the bridge aperture are sized and configured to facilitate the circulation of air over the back surfaces of the lenses to resist the fogging thereof.

* * * * *